(12) United States Patent
Jeong et al.

(10) Patent No.: US 9,297,781 B2
(45) Date of Patent: Mar. 29, 2016

(54) ELECTRODE SYSTEM AND METHOD FOR CALCULATING CHARACTER VALUES OF SOLUTION USING THE SAME

(71) Applicant: SAMSUNG ELECTRONICS CO., LTD., Suwon-si, Gyeonggi-do (KR)

(72) Inventors: Yong Won Jeong, Seoul (KR); Yong Soo Lee, Seoul (KR); Young Chul Ko, Suwon (KR)

(73) Assignee: SAMSUNG ELECTRONICS CO, LTD., Suwon-Si (KP)

( * ) Notice: Subject to any disclaimer, the term of this patent is extended or adjusted under 35 U.S.C. 154(b) by 625 days.

(21) Appl. No.: 13/650,809

(22) Filed: Oct. 12, 2012

(65) Prior Publication Data

US 2013/0092560 A1    Apr. 18, 2013

(30) Foreign Application Priority Data

Oct. 14, 2011 (KR) .................. 10-2011-0105514
May 21, 2012 (KR) .................. 10-2012-0053490

(51) Int. Cl.
*G01N 27/416* (2006.01)

(52) U.S. Cl.
CPC .................................. *G01N 27/4168* (2013.01)

(58) Field of Classification Search
CPC ....................................................... G01N 27/30
See application file for complete search history.

(56) References Cited

U.S. PATENT DOCUMENTS

| | | | | |
|---|---|---|---|---|
| 4,602,985 A | * | 7/1986 | Hough et al. | 205/411 |
| 5,746,900 A | * | 5/1998 | Venkatasetty | G01N 27/4045 204/412 |
| 6,718,628 B2 | * | 4/2004 | Munshi | 29/825 |
| 6,974,533 B2 | * | 12/2005 | Zhou | 205/264 |
| 2004/0146786 A1 | * | 7/2004 | Sato et al. | 429/326 |
| 2007/0289870 A1 | * | 12/2007 | Nair et al. | 204/424 |
| 2008/0166599 A1 | * | 7/2008 | Swathirajan | H01M 4/8605 429/429 |
| 2010/0051480 A1 | * | 3/2010 | Schoenfisch et al. | 205/781 |
| 2010/0126858 A1 | * | 5/2010 | Saito et al. | 204/403.14 |
| 2010/0280347 A1 | * | 11/2010 | Shah | C12Q 1/006 600/347 |
| 2012/0123318 A1 | * | 5/2012 | Ek et al. | 604/20 |
| 2014/0224671 A1 | * | 8/2014 | Koide | 205/777.5 |

FOREIGN PATENT DOCUMENTS

KR    10-0481663    3/2005

OTHER PUBLICATIONS

Park et al. (Proceedings of the 3rd IEEE Int. Conf. 2008).*
Kasem (Platinum Metals Rev., 2008, 52, (2), 100).*
Carpenter et al. (ANWER/TM-3 1994).*
Partial European Search Report mailed Jan. 21, 2013 for corresponding European Application No. 12188401.9.
Gibeault Jean-Pierre et al., "New Instruments to Measure and Monitor Dissolved Hydrogen in Water", Transactions of the American Nuclear Society, vol. 46, Jan. 1, 1984, XP008159218, ISSN: 0003-018X, pp. 612-613.

(Continued)

*Primary Examiner* — Jennifer Dieterle
(74) *Attorney, Agent, or Firm* — Staas & Halsey LLP

(57) ABSTRACT

An electrode system for measuring properties of solutions using a porous platinum electrode. The electrode system includes a low porosity platinum working electrode in which platinum is deposited in a porous form on the surface of an electrode, and a high porosity platinum electrode having a higher roughness factor than the low porosity platinum electrode.

8 Claims, 12 Drawing Sheets

(56) References Cited

OTHER PUBLICATIONS

R.D. Prien et al., "Development and first results of a new mesoporous microelectrode D0-sensor", MTS/IEEE Oceans 2001, An Ocean Odyssey, Conference Proceedings (IEEE Cat. No. 01CH37295), vol. 3, Jan. 1, 2001, pp. 1910-1914, XP55049325, DOI: 10.1109/Oceans. 2001.968138, ISBN: 978-0-93-395728-2.

Jae Lee Yi et al., "A Highly Miniaturized Dissolved Oxygen Sensor Using a Nanoporous Platinum Electrode Electroplated on Silicon", Journal of the Korean Physical Society, vol. 58, No. 52, May 13, 2011, pp. 1505-1510, XP55049314, ISSN: 0374-4884, DOI: 10.3938/jkps.58.1505.

Changhe Wen et al., "Voltammetry in Solution Isolated in a Porous Platinum Electrode", Journal of the Electrochemical Society, vol. 144, No. 3, Jan. 1, 1997, pp. 884-888, XP55049326.

S.M. Piovano et al., "The influence of electrode structure on the adsorption and electro-oxidation of ethylene on platinum", Journal of Applied Electrochemistry, vol. 17, No. 1, Jan. 1, 1987, pp. 147-155, XP55049308, ISSN: 0021-891X, DOI: 10.1007/bf01009141.

* cited by examiner

ELECTRODE SYSTEM AND METHOD FOR CALCULATING CHARACTER VALUES OF SOLUTION USING THE SAME

CROSS-REFERENCE TO RELATED APPLICATIONS

This application claims the benefit of Korean Patent Application Nos. 10-2011-0105514 and 10-2012-0053490, filed on Oct. 14, 2011 and May 21, 2012, respectively, in the Korean Intellectual Property Office, the disclosures of which are incorporated herein by reference.

BACKGROUND

1. Field

Embodiments of the present disclosure relate to an electrode system. More specifically, embodiments of the present disclosure relate to an electrode system using a porous platinum electrode and a method for calculating pH, oxidation-reduction potential or the like of a solution using the same.

2. Description of the Related Art

An oxidation-reduction potential (ORP) sensor used in the related art is optimized for measurement of oxidation-reduction potentials of ions in a solution.

Accordingly, there is a problem in that it is difficult to obtain stable values in measurement of an oxidation-reduction potential of a gas dissolved in a solution, for example, a reducing gas such as hydrogen gas or oxidizing gas such as oxygen gas.

The reason for this is that a bonding force between a platinum electrode and a gas dissolved in a solution is lower than a bonding force between the platinum electrode and ions present in the solution.

Further, during actual measurement, when vibration is applied to electrodes or agitation such as stirring is applied to the solution to be measured by surroundings or other factors, it is more difficult to obtain accurate values.

Also, since the measured values depend on the surface of a platinum electrode due to low bonding force, a great deviation of 200 to 300 mV in measured value between sensors disadvantageously occurs or a great deviation occurs in spite of using the same sensor according to use history.

SUMMARY

Therefore, it is one aspect of the present disclosure to provide an electrode system capable of more accurately measuring properties of solutions using a porous platinum electrode.

Also, it is another aspect to provide an electrode system capable of detaching hydrogen atoms bonded to a platinum electrode, in order to prevent deterioration in the platinum electrode caused by bonding between the platinum electrode and the hydrogen atoms.

Additional aspects will be set forth in part in the description which follows and, in part, will be obvious from the description, or may be learned by practice of the invention.

In accordance with one aspect, provided is an electrode system including: a low porosity platinum electrode in which platinum is deposited in a porous form on the surface of an electrode; and a high porosity platinum electrode having a higher roughness factor than the low porosity platinum electrode.

The low porosity platinum electrode may have a roughness factor of about 1 to about 50 and the high porosity platinum electrode may have a roughness factor of about 50 to about 400.

The electrode system may further include an additional reference electrode.

The reference electrode may be made of gold or silver.

The low porosity platinum electrode and the high porosity platinum electrode may be working electrodes with respect to the reference electrode and the low porosity platinum electrode may be an oxidation-reduction potential (ORP) measurement electrode and the high porosity platinum electrode may be a pH measurement electrode.

The low porosity platinum electrode may be a working electrode that measures an oxidation-reduction potential of a solution using the high porosity platinum electrode as a reference electrode.

The oxidation-reduction potential calculated by the low porosity platinum electrode using the high porosity platinum electrode as a reference electrode may be an oxidation-reduction potential based on a dissolved gas present in the solution.

The solution may be reducing water in which hydrogen gas is dissolved and the dissolved gas may contain a hydrogen gas.

In accordance with another aspect, provided is a method for calculating a character value of a solution using an electrode system including a high porosity platinum electrode and a low porosity platinum electrode, including: calculating an oxidation-reduction potential of a solution from the low porosity platinum electrode using the high porosity platinum electrode as a reference electrode; and calculating a concentration of dissolved gas in the solution from the calculated oxidation-reduction potential of the solution.

The low porosity platinum electrode may have a roughness factor of about 1 to about 50 and the high porosity platinum electrode may have a roughness factor of about 50 to about 400.

The oxidation-reduction potential calculated by the low porosity platinum electrode using the high porosity platinum electrode as a reference electrode may be an oxidation-reduction potential based on a dissolved gas present in the solution.

The electrode system may further include an additional reference electrode.

The reference electrode may be made of gold or silver.

The oxidation-reduction potential of the solution may be calculated using the low porosity platinum electrode as the working electrode with respect to the additional reference electrode, and pH may be calculated using the high porosity platinum electrode as the working electrode with respect to the additional reference electrode.

The solution may be reducing water in which hydrogen gas is dissolved and the dissolved gas may contain a hydrogen gas.

The character value of the solution may include pH and oxidation-reduction potential of the solution, and concentration of dissolved gas in the solution.

In accordance with another aspect, provided is an electrode system including: an electrode unit including a reference electrode and a platinum working electrode; a power unit to apply a voltage to the electrode unit; a readout device to calculate a character value of a solution through an output value of the electrode unit; a relay to electrically connect the electrode unit to the power unit or the readout device; and a control unit to control the relay such that the electrode unit is electrically connected to the power unit, based on the output value of the readout device.

The control unit may control the relay such that the electrode unit is electrically connected to the power unit, when the output value of the readout device exceeds a predetermined reference value.

The control unit may control the relay such that the electrode unit is electrically connected to the power unit at a predetermined interval.

The power unit may apply a positive voltage to the platinum working electrode when the power unit is electrically connected to the electrode unit.

The power unit may apply a voltage of about 0V to about 2V to the platinum working electrode.

The platinum working electrode may include a low porosity platinum electrode and a high porosity platinum electrode.

According to one aspect, it is possible to more accurately measure an oxidation-reduction potential of a dissolved hydrogen gas in reducing water and calculate the concentration of the dissolved hydrogen gas.

Also, it is possible to prevent deterioration in performance of the platinum electrode caused by bonding the platinum electrode and hydrogen atoms that may occur when immersed in reducing water for a long period of time.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, embodiments of the present disclosure will be described with reference to the accompanying drawings.

Figure 1:
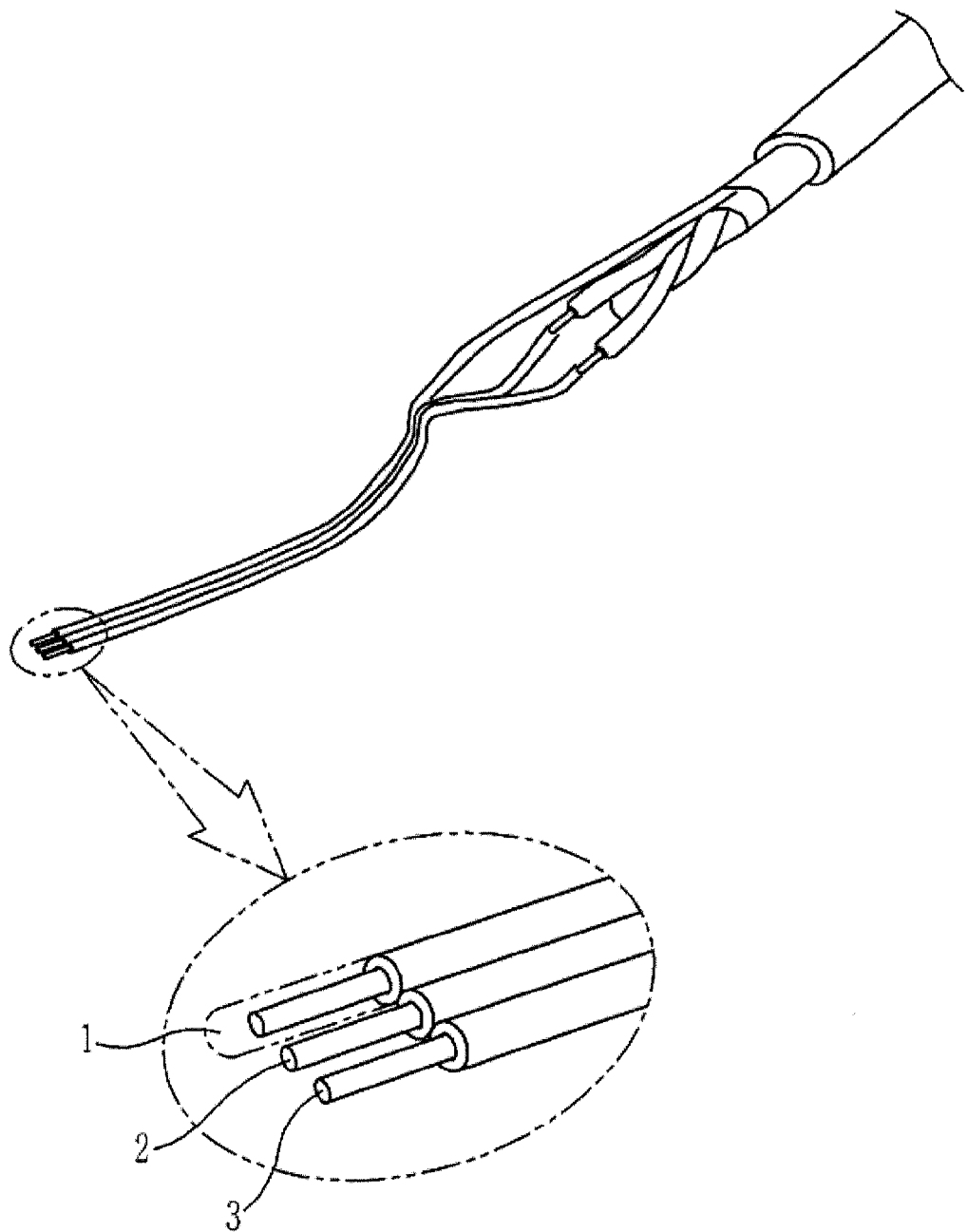
FIG. 1 is a view illustrating an electrode system according to one embodiment.

FIG. 1 is a view illustrating an electrode system according to one embodiment. The electrode system according to one embodiment includes a reference electrode 1 and two working electrodes.

The electrode system according to one embodiment is used to measure pH or oxidation-reduction potential of a solution. More specifically, the electrode system may be used for calculation of a pH or an oxidation-reduction potential of reducing water or a dissolved hydrogen gas concentration of reducing water. Further, the electrode system may be used for calculation of concentrations of various gases dissolved in the solution to be measured.

The reference electrode 1 may be gold (Au) or silver (Ag) and is preferably formed using gold that does not substantially exhibit reactivity in the solution to be measured. The reference electrode 1 serves as a basis of potential calculation of the two working electrodes.

The two working electrodes are porous platinum electrodes formed by depositing platinum in a porous form on the surface of general bulk platinum or other metal.

The porous platinum may be deposited using electropolymerization. The porous platinum electrode thus obtained exhibits a great increase in overall surface area according to the processed thickness. The surface area of the porous platinum electrode represented by roughness factor (Rf) increases to 400 times, assuming that Rf of general platinum is 1.

Figure 2:
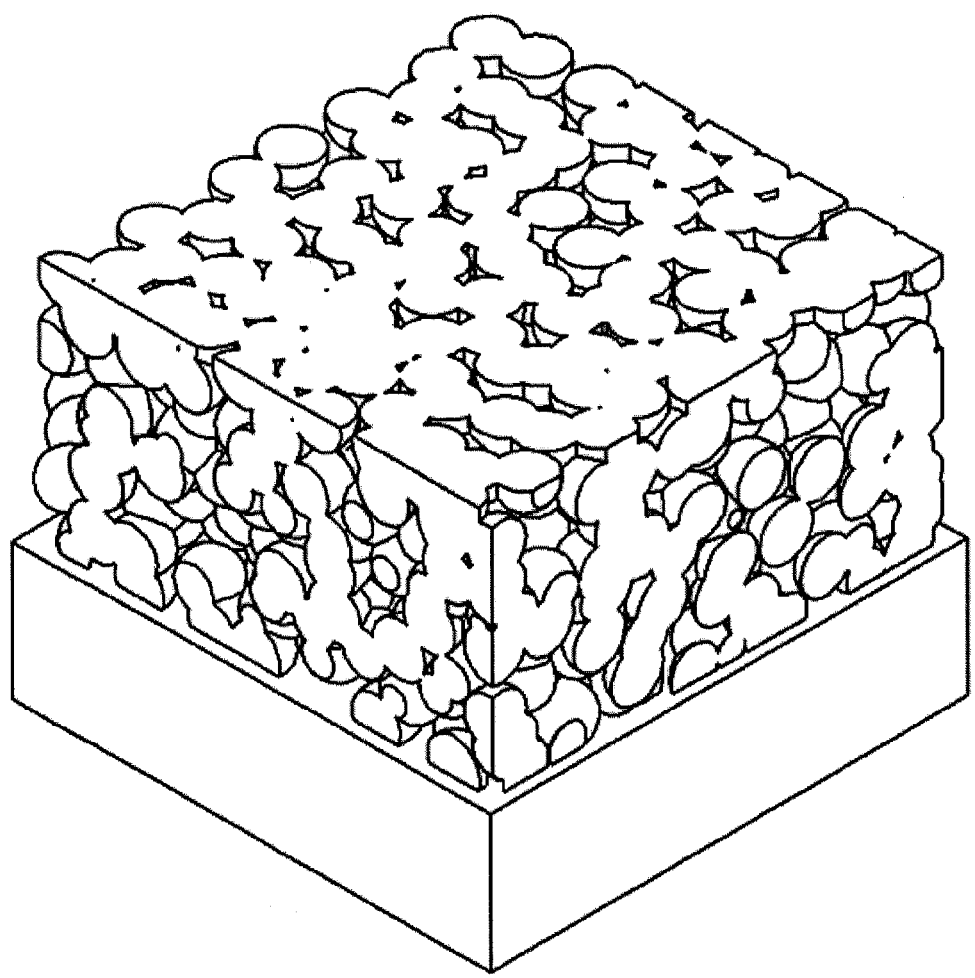
FIG. 2 is a view illustrating the surface of a porous platinum electrode.
Figure 3:
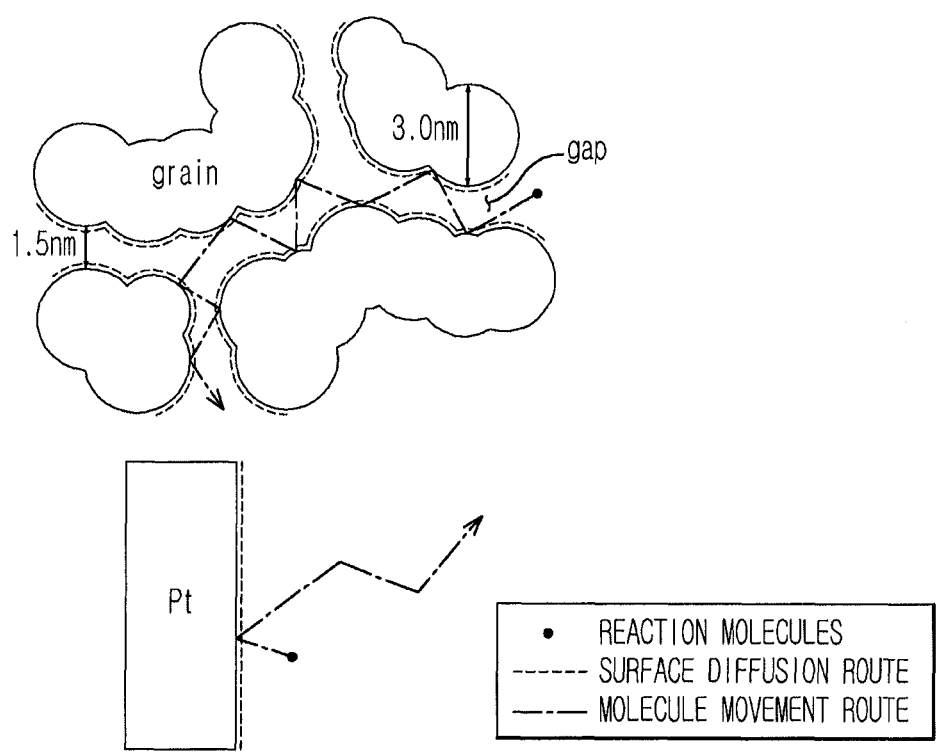
FIG. 3 is a concept view illustrating a reaction state of reactant substances in the porous platinum electrode according to one embodiment.

FIG. 2 is a view illustrating the surface of a porous platinum electrode. FIG. 3 is a concept view illustrating a reaction state of a subject to be measured in the porous platinum electrode according to one embodiment.

For more accurate observation, when the surface state of porous platinum is observed by transmission electron microscopy (TEM), the size of platinum grain is about 3 nm and the gap between grains has a size of about 1 to about 2 nm.

The two porous platinum electrodes may have different porosities. One is a porous platinum electrode having Rf of 1 to 50 (hereinafter, referred to as a low porosity platinum electrode), which may be a porous platinum electrode having a low deposition degree of porous platinum or a general platinum electrode.

The other platinum electrode is a porous platinum electrode that has Rf of 50 to 400 (hereinafter, referred to as a "high porous platinum electrode").

In a case in which there occurs variation in concentration of a substance in need of measurement, for example, ions such as hydrogen ions or molecules such as dissolved hydrogen gas, contained in a solution to be measured, the general platinum electrode or the low porosity platinum electrode 2 yields measurement results to which the variation is applied, while the high porosity platinum electrode 3 does not yield measurement results to which the variation is applied.

For example, in an electrical-reduction water production device, dissolved hydrogen gas evaporates from reducing water stored in a water tank and, as a result, the concentration of hydrogen gas decreases.

Figure 4:
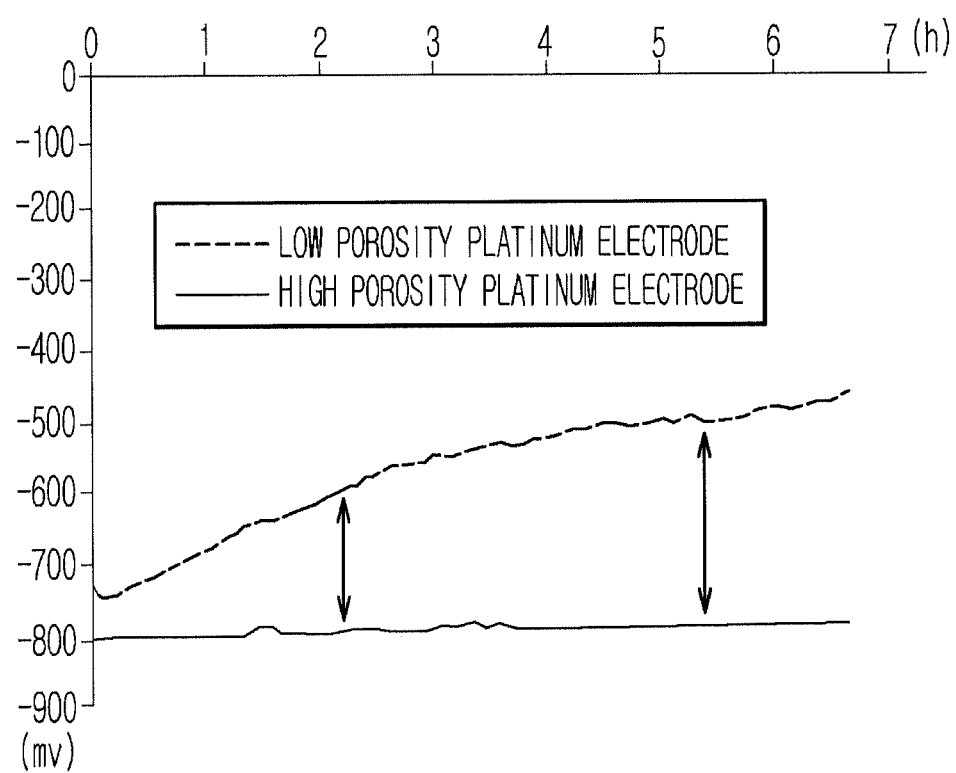
FIG. 4 is a graph showing measured values of oxidation-reduction potential of the porous platinum electrode according to one embodiment.

The oxidation-reduction potential value measured from the general platinum electrode or low porous platinum electrode 2 increases in proportion to a decreased concentration of hydrogen gas, while the oxidation-reduction potential value measured from the high porosity platinum electrode 3 has a constant oxidation-reduction potential, regardless of concentration variation in hydrogen gas (see FIG. 4).

FIG. 4 is a graph showing a result of a measured value of oxidation-reduction potential of the porous platinum electrode according to one embodiment. FIG. 4 shows a measured value of an oxidation-reduction potential of a low porosity platinum electrode 2 and a measured value of an oxidation-reduction potential of a high porosity platinum electrode 3 in reducing water at pH 9.9. The graph of oxidation-reduction potential of the high porosity platinum electrode 3 exhibits a constant oxidation-reduction potential, regardless of evaporation of dissolved hydrogen gas as time goes by, while the graph of oxidation-reduction potential of the low porosity platinum electrode 2 exhibits an increase in oxidation-reduction potential, to which a decrease in dissolved hydrogen gas concentration caused by evaporation of dissolved hydrogen gas is applied. The high porosity platinum electrode 3 has a gap between grains of 5 nm or less. When a molecule such as hydrogen gas is introduced into the gap, the hydrogen gas passes through the gap and, at the same time, is scattered, and then reacts with grains surrounding the gap several times.

Such a multiple reaction exhibits the same effects as in the case in which a plurality of particles are introduced, in spite of using one particle.

As can be seen from FIG. 3, reaction molecules introduced into the gap of the high porosity platinum electrode 3 occur multiple reactions while moving along the gap, while, in a general platinum electrode, one molecule undergoes only one reaction. Accordingly, although the concentration of dissolved hydrogen gas decreases due to evaporation of hydrogen gas from reducing water of the water tank, a measured value of an oxidation-reduction potential of the high porosity platinum electrode 3 has an approximate maximum value, regardless of the concentration variation of dissolved hydrogen gas, as long as the concentration of dissolved hydrogen gas do not decrease to a predetermined level.

However, since ions such as hydrogen ions move along the surface of platinum through surface diffusion, they do not react with grains surrounding the gaps like molecules such as hydrogen gas several times and move along one grain surface through surface diffusion, although they are introduced into the gap between grains of the high porosity platinum electrode 3 (see FIG. 3).

Accordingly, all of the general platinum electrode, the low porosity platinum electrode 2, and the high porosity platinum electrode 3 yield measured values of oxidation-reduction potential to which concentration variation of hydrogen ions is applied.

Thus, the low porosity platinum electrode 2 of the electrode system according to one embodiment of the present invention may be used as an electrode for measuring an oxidation-reduction potential of a solution to be measured.

The oxidation-reduction potential is a sum of oxidation-reduction potentials that oxidizing/reducing substances affect electrodes and should reflect the effects of both hydrogen ions and dissolved hydrogen gas, for example, when the hydrogen ions and dissolved hydrogen gas are present as oxidizing/reducing substances in a solution to be measured.

Accordingly, as described above, when variation in concentration of dissolved hydrogen gas occurs, the low porosity platinum electrode 2 that can yield measurement results reflecting the variation is used as an oxidation-reduction potential measurement electrode.

Meanwhile, the high porosity platinum electrode 3 is used as a pH measurement electrode of a solution to be measured since it is not affected by variation in concentration of the dissolved hydrogen gas and is affected only by hydrogen ion concentration. The electrode system according to one embodiment of the present invention enables oxidation-reduction potential and pH of a solution to be measured.

The oxidation-reduction potential of highly active reducing water includes a reducing force of the dissolved hydrogen gas as well as an oxidizing force of hydrogen ions. For this reason, in order to accurately evaluate the reducing force of dissolved hydrogen gas of reducing water, the effect of the oxidizing force of hydrogen ions should be excluded.

The electrode system according to one embodiment of the present invention can accurately calculate an oxidation-reduction potential of dissolved gas present in the solution to be measured using two porous platinum electrodes having different porosities, that is, the low porosity platinum electrode 2 and the high porosity platinum electrode 3 and concentration of dissolved gas using the same. The high porosity platinum electrode 3 and the low porosity platinum electrode 2 have the same reactivity to ions, for example, hydrogen ions of a solution to be measured. That is, they calculate measured values of oxidation-reduction potentials to which variation in concentration of hydrogen ions is applied.

The high porosity platinum electrode 3 exhibits a constant measured value of an oxidation-reduction potential, regardless of variation in concentration of dissolved hydrogen gas, while the low porosity platinum electrode 2 exhibits a measured value of an oxidation-reduction potential, to which a concentration variation of dissolved hydrogen gas is applied (see FIG. 4).

Accordingly, when a measured value of an oxidation-reduction potential is calculated using the high porosity platinum electrode 3 as a reference electrode and the low porosity platinum electrodes 2 as working electrodes, the high porosity platinum electrode 3 and the low porosity platinum electrode 2 calculate measured values of an oxidation-reduction potential to which concentration variation of hydrogen ions is applied, thus obtaining measured values of an oxidation-reduction potential in which the effect of hydrogen ions of the solution to be measured is offset and only the effect of dissolved hydrogen gas is reflected.

In highly active reducing water, it is important to measure the reducing force of dissolved hydrogen gas dissolved in reducing water. In this regard, the electrode system according to one embodiment can calculate measured values of an oxidation-reduction potential in which only the effect of dissolved hydrogen gas of reducing water is reflected, thus more accurately measuring the reducing force of dissolved hydrogen gas as well as the concentration of dissolved hydrogen gas in reducing water, based on the oxidation-reduction potential of dissolved hydrogen gas.

Figure 5:
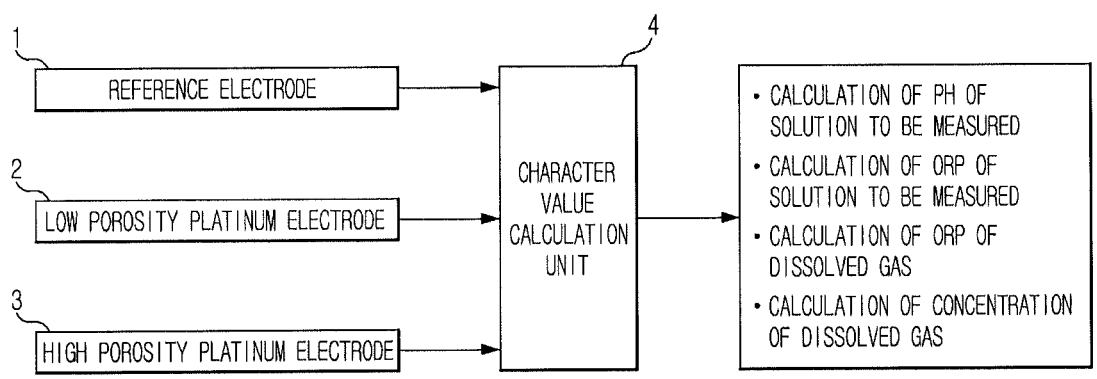
FIG. 5 is a block diagram illustrating a configuration to calculate character values of a solution in an electrode system according to one embodiment.

FIG. 5 is a block diagram illustrating a configuration to calculate character values of a solution in an electrode system according to one embodiment.

The solution character value calculation unit 4 calculates information exhibiting properties such as oxidation-reduction potential and pH of solutions through potentials of the high porosity platinum electrode 3 and the low porosity platinum electrode 2. The solution character value calculation unit 4 may be a readout device.

The solution character value calculation unit 4 calculates an oxidation-reduction potential of a solution through the potential value of the low porosity platinum electrode 2 to the reference electrode 1. The oxidation-reduction potential of the solution thus calculated exhibits an oxidation-reduction potential to which effects of both ions and dissolved gases present in the solution are applied. The oxidation-reduction potential is a sum of oxidation-reduction potentials that oxidizing/reducing substances and should reflect the effects of both hydrogen ions and dissolved hydrogen gas, for example, when the hydrogen ions and dissolved hydrogen gas are present as oxidizing/reducing substances in a solution to be measured. Accordingly, as described above, when variation in concentration of dissolved hydrogen gas occurs, the low porosity platinum electrode 2 that can yield measurement results to which the variation is applied is used as an oxidation-reduction potential measurement electrode.

The solution character value calculation unit 4 calculates pH of a solution based on the potential value of the high porosity platinum electrode 3 to the reference electrode 1. As described above, the high porosity platinum electrode 3 is used as a pH measurement electrode of a solution to be measured, since it is not affected by variation in concentration of dissolved hydrogen gas and is affected by only concentration of hydrogen ions.

The solution character value calculation unit 4 calculates measured values of an oxidation-reduction potential through the potential value of the low porosity platinum electrode 2 to the high porosity platinum electrode 3 using the high porosity platinum electrode 3 as a reference electrode and the low porosity platinum electrodes 2 as working electrodes. As a result, the oxidation-reduction potential in which only the effect of dissolved hydrogen gas is reflected is obtained, since the effect of hydrogen ions of the solution to be measured is offset.

Also, the solution character value calculation unit 4 calculates concentration of dissolved gas in a solution through the calculated oxidation-reduction potential of the solution.

In highly active reducing water, it is important to measure the reducing force of hydrogen gas dissolved in reducing water. In this regard, an oxidation-reduction potential in which only the effect of dissolved hydrogen gas of reducing water is reflected, is calculated through the potential value of the low porosity platinum electrode 2 calculated using the high porosity platinum electrode 3 as a reference electrode, thereby more accurately measuring the reducing force of dissolved hydrogen gas as well as the concentration of dissolved hydrogen gas in reducing water, based on the oxidation-reduction potential.

Figure 6A:
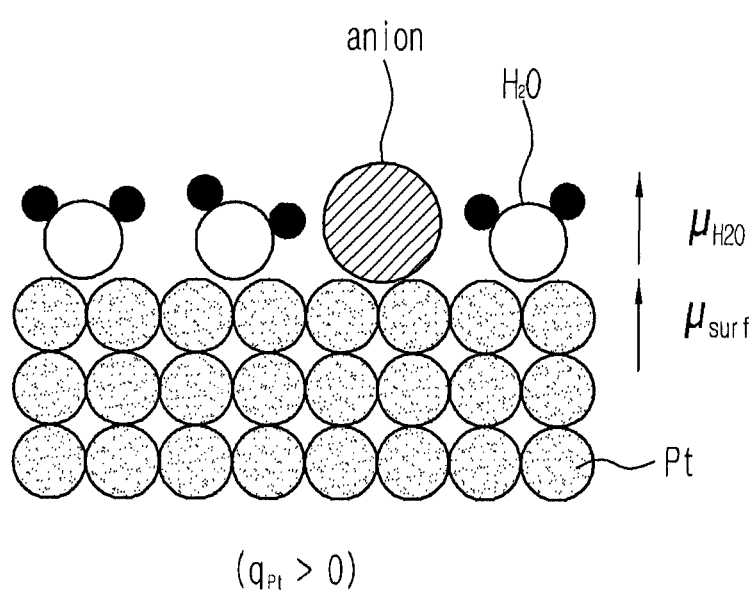
FIGS. 6A and 6B are views illustrating reaction on the surface of the platinum electrode according to surface potentials of the platinum electrode.
Figure 6B:
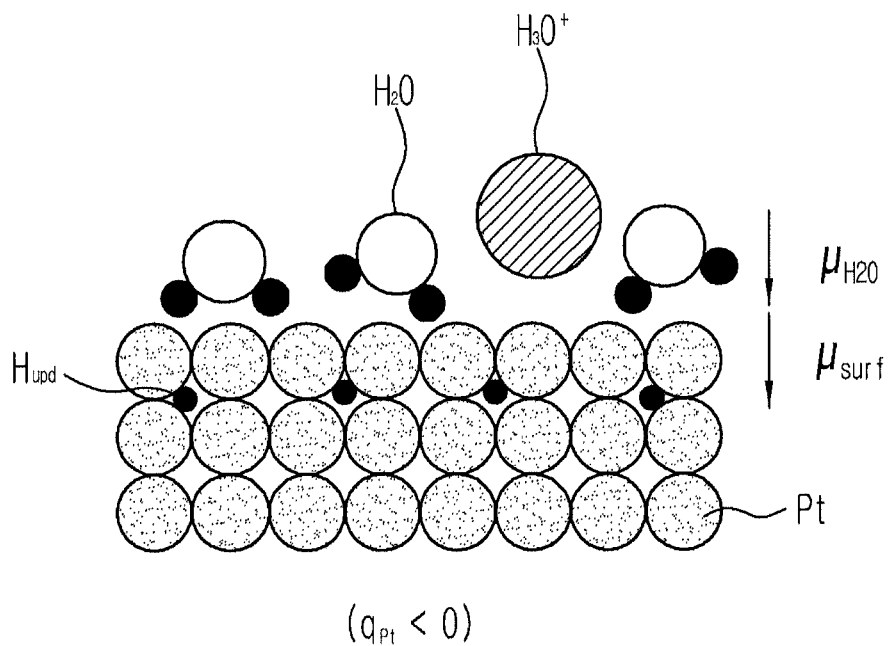

FIGS. 6A and 6B are views illustrating reactions on the surface of a platinum electrode according to surface potential of the platinum electrode.

When an oxidation-reduction potential of the platinum electrode including a low porosity platinum electrode 2 and a high porosity platinum electrode 3 according to one embodiment is measured while immersing the platinum electrode in highly active reducing water containing a great amount of dissolved hydrogen gases for a long period of time, dissolved hydrogen gases and hydrogen atoms in water molecules continuously react with platinum. When this reaction occurs for a long period of time, hydrogen atoms are accumulated in platinum and reactivity of hydrogen gas to platinum thus decreases.

Referring to FIG. 6A, when the surface potential of the platinum electrode is a positive value ($q_{pt}>0$), a dipole moment ($\mu_{surf}$) of the platinum electrode surface directs toward a surface direction of the platinum electrode.

In this case, the surface of the platinum electrode contacts oxygen molecules of water molecules and reaction between platinum and hydrogen atoms does not occur.

Referring to FIG. 6B, when the surface potential of the platinum electrode is a negative value ($q_{pt}<0$), a dipole moment ($\mu_{surf}$) of the platinum electrode surface directs toward an opposite direction to a surface direction of the platinum electrode.

In this case, the surface of the platinum electrode contacts hydrogen atoms of water molecules and dissolved hydrogen gas. As time passes in this state, hydrogen atoms of water molecules sand dissolved hydrogen gas react with electrons present on the platinum surface, hydrogen atoms are produced even at a voltage or less at which electrolysis actually occurs, which are adsorbed on the platinum surface.

Such a hydrogen atom is referred to as underpotential deposition hydrogen, represented by "$H_{upd}$".

In highly active reducing water, the potential of platinum electrode surface is about −600 mV to about −500 mV, with respect to the reference electrode 1 and the surface charge of the platinum electrode thus maintains a negative value. Under this condition, the electrode is immersed for a long period of time, $H_{upd}$ adsorbed on the platinum surface increases and performance of electrode is thus deteriorated. Accordingly, the embodiment of the present invention provides an electrode system that returns the platinum electrode on which hydrogen atoms are adsorbed while being exposed in a state of FIG. 6B for a long period of time to the state of FIG. 6A.

Figure 7:
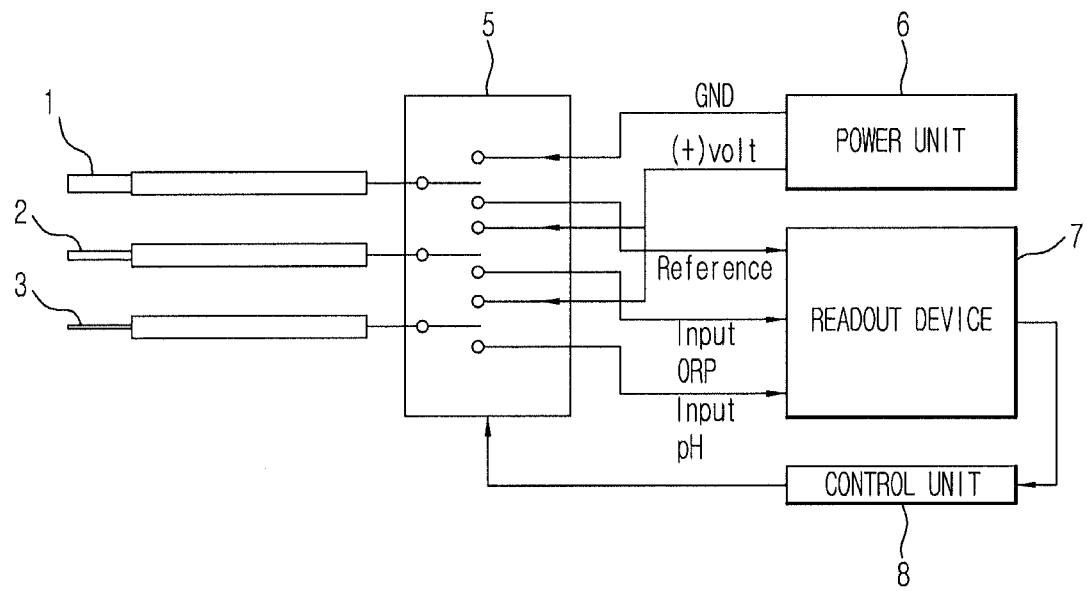
FIG. 7 is a view illustrating a configuration of an electrode system to recycle the platinum electrode according to one embodiment.

FIG. 7 is a view illustrating a configuration of an electrode system to recycle the platinum electrode according to one embodiment.

The electrode system includes an electrode unit including a reference electrode 1, a low porosity platinum electrode 2 and a high porosity platinum electrode 3, a relay 5 to selectively connect the electrode unit to a power unit or a readout device 7, the power unit 6 to supply power to the electrode unit, a readout device 7 to calculate an oxidation-reduction potential or pH of a solution according to a measured value of the electrode unit, and a control unit 8 to control driving of the relay 5 based on the calculated result of the readout device 7.

Under general conditions in which the electrode unit measures properties of solutions, the relay 5 electrically connects the electrode unit to the readout device 7.

In this case, as described above, since the low porosity platinum electrode 2 is used as an oxidation-reduction potential measurement electrode that measures an oxidation-reduction potential of a solution, an output value of the low porosity platinum electrode 2 means an oxidation-reduction potential of a solution.

Also, both the high porosity platinum electrode 3 and the low porosity platinum electrode 2 calculate a measured value of an oxidation-reduction potential reflecting concentration variation of hydrogen ions. Accordingly, the oxidation-reduction potential measured using the high porosity platinum electrode 3 as a reference electrode and the low porosity platinum electrode 2 as a working electrode means an oxidation-reduction potential in which only the effect of dissolved hydrogen gas is reflected.

Also, as described above, the output value of the high porosity platinum electrode 3 means pH of the solution, since it is not affected by variation in concentration of the dissolved hydrogen gas in the solution to be measured and is affected only by the concentration of hydrogen ions.

When hydrogen atoms are adsorbed on the platinum surface and, as a result, measurement performance of the platinum electrode is deteriorated, after the electrode unit is immersed in the solution to be measured for a long period of time, the control unit 8 controls the relay 5 so that the electrode unit is electrically connected to the power unit 6.

When the electrode unit is electrically connected to the power unit 6, a positive potential is applied to the platinum electrode, with respect to the reference electrode 1.

When the positive potential is applied from the outside to the platinum electrode, the surface potential of platinum electrode is a positive value ($q_{pt}>0$), hydrogen atoms adsorbed on the platinum surface are detached from the platinum surface.

When hydrogen atoms are detached, the measurement performance of the platinum electrode is recovered and the problem of performance deterioration is thus solved. Hereinafter, a process in which hydrogen atoms adsorbed on the platinum electrode are detached by applying a positive voltage to the platinum electrode to recover measurement performance of the platinum electrode will be referred to as an "oxidation recycling".

The voltage applied for oxidation recycling of the platinum electrode may be a value of 0 to 2V with respect to the reference electrode 1. Also, the time for which a voltage is applied is preferably 1 to 30 minutes. However, the level of voltage applied to the platinum electrode may be varied depending on the oxidation-reduction potential of a subject in need of measurement and a voltage application time may be varied depending on surface area of platinum.

The control unit 8 monitors output of the readout device 7 and thereby determines a control time of the relay 5. That is, the control unit 8 increases the potential of the platinum electrode, when hydrogen atoms are adsorbed on the surface of the platinum electrode, and the control unit 8 controls the relay 5 so that the platinum electrode is connected to the power unit 6, when the potential of the platinum electrode exceeds a predetermined reference value.

Alternatively, a predetermined time after the platinum electrode is immersed in reducing water, the control unit 8 controls the relay 5 so that the platinum electrode is connected to the power unit 6.

Figure 8:
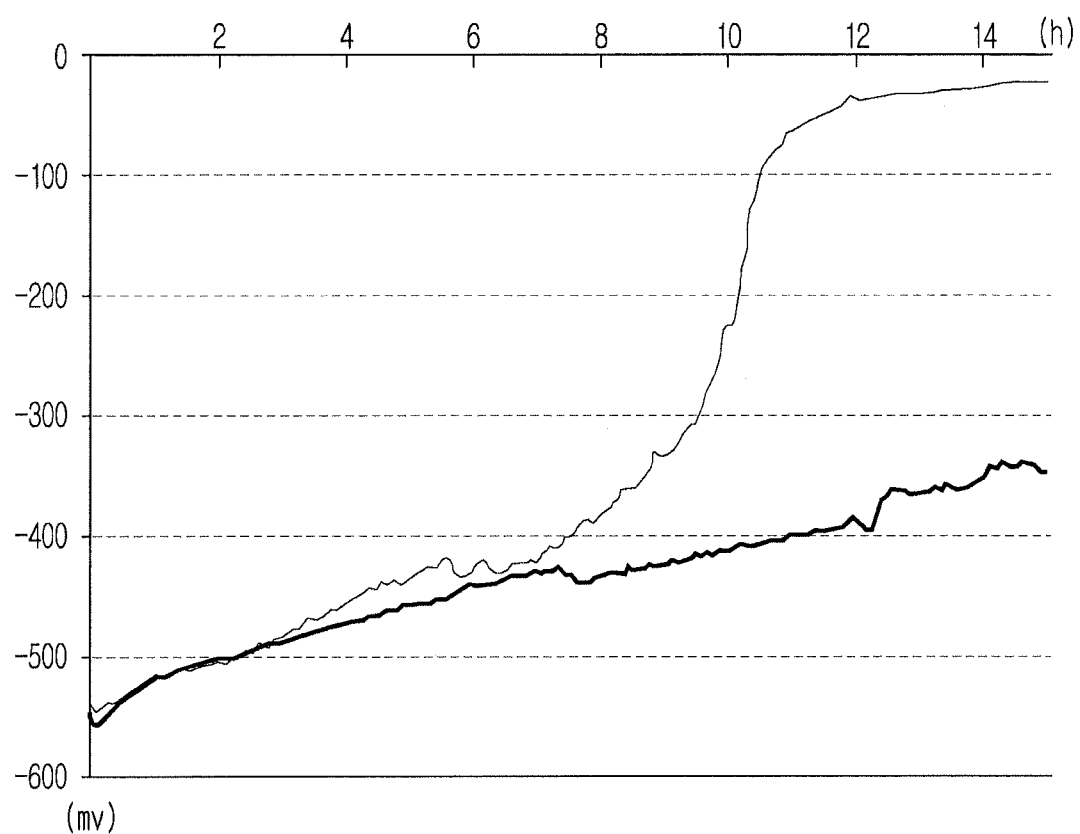
FIGS. 8 to 11 are graphs showing variation in oxidation-reduction potential of platinum electrode as a function of time.

FIG. 8 is a graph showing an oxidation-reduction potential of an initial platinum electrode and an oxidation-reduction potential of a platinum electrode immersed in reducing water for three days.

A thick line represents variation in initial oxidation-reduction potential of the platinum electrode and a thin line represents variation in oxidation-reduction potential of the platinum electrode immersed in reducing water for three days.

When the platinum electrode is immersed in reducing water for several days, the surface potential of the platinum electrode that has a negative value due to high reducing force of the reducing water causes an increase in hydrogen atoms adsorbed on platinum, thus causing a rapid increase in oxidation-reduction potential value of the platinum electrode. The increase in oxidation-reduction potential of initial platinum electrode over time is a natural result that reflects evaporation of dissolved hydrogen gas.

Figure 9:
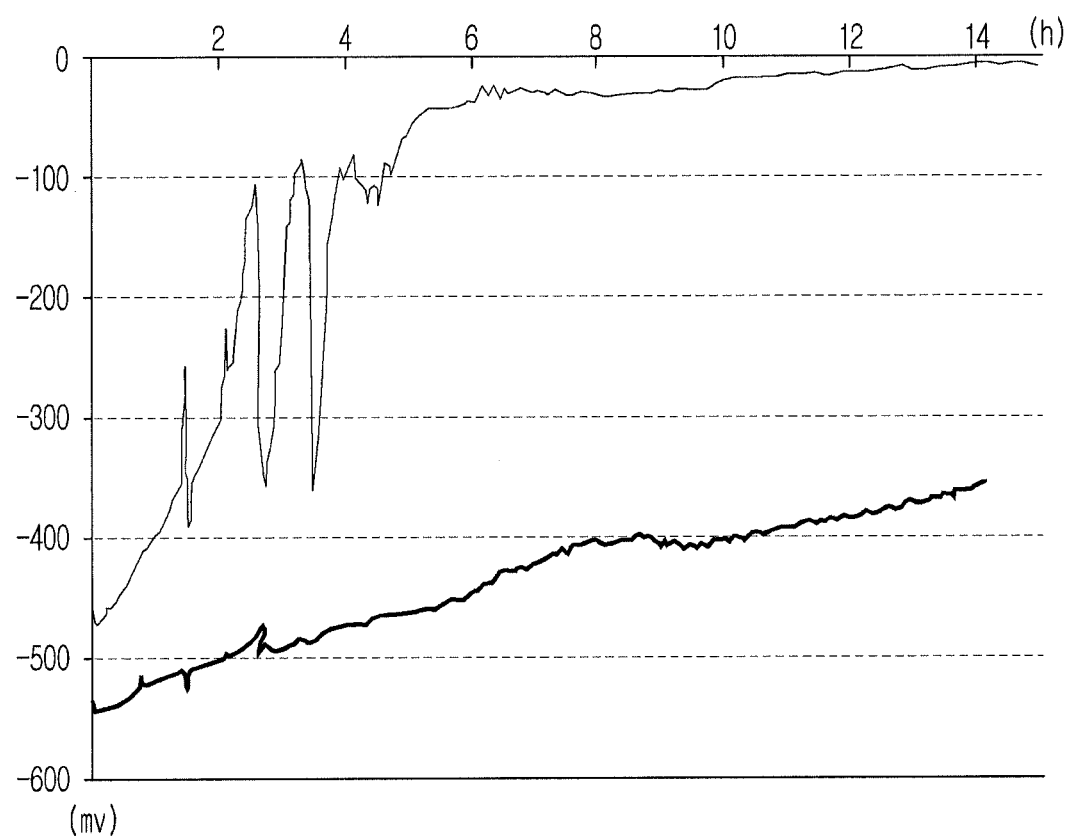

FIG. 9 is a graph showing an oxidation-reduction potential of the platinum electrode oxidation-recycled after immersion for one day and an oxidation-reduction potential of the platinum electrode immersed in reducing water for four days.

It can be seen that the variation (thin line) in oxidation-reduction potential of the platinum electrode immersed for four days is sharper than variation in oxidation-reduction potential of the platinum electrode immersed for three days shown in FIG. 8.

On the other hand, there is no great difference between variation in oxidation-reduction potential of the platinum electrode oxidation-recycled after immersion for one day (thick line) and variation in oxidation-reduction potential of the initial platinum electrode of FIG. 8.

Figure 10:
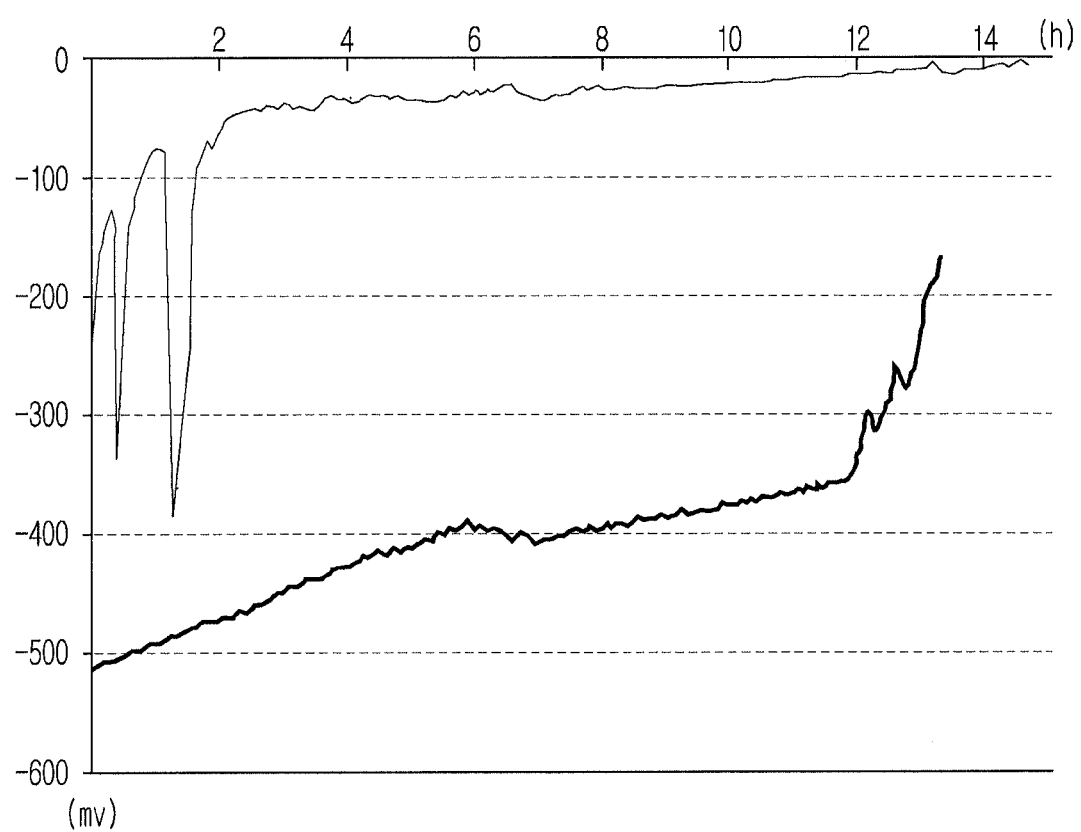

FIG. 10 is a graph showing an oxidation-reduction potential of the platinum electrode oxidation-recycled after immersion for two days and an oxidation-reduction potential of platinum electrode immersed in reducing water for five days.

The variation (thin line) in oxidation-reduction potential of the platinum electrode immersed for five days means a saturated state in which hydrogen atoms are adsorbed on the surface of the platinum electrode and the oxidation-reduction potential value thus reaches about 0 mV.

On the other hand, there is no great difference between variation in oxidation-reduction potential (thick line) of the platinum electrode oxidation-recycled after immersion for two days, variation in oxidation-reduction potential of the initial platinum electrode of FIG. 8 and variation in oxidation-reduction potential (thick line) of the platinum electrode oxidation-recycled after immersion for one day.

Figure 11:
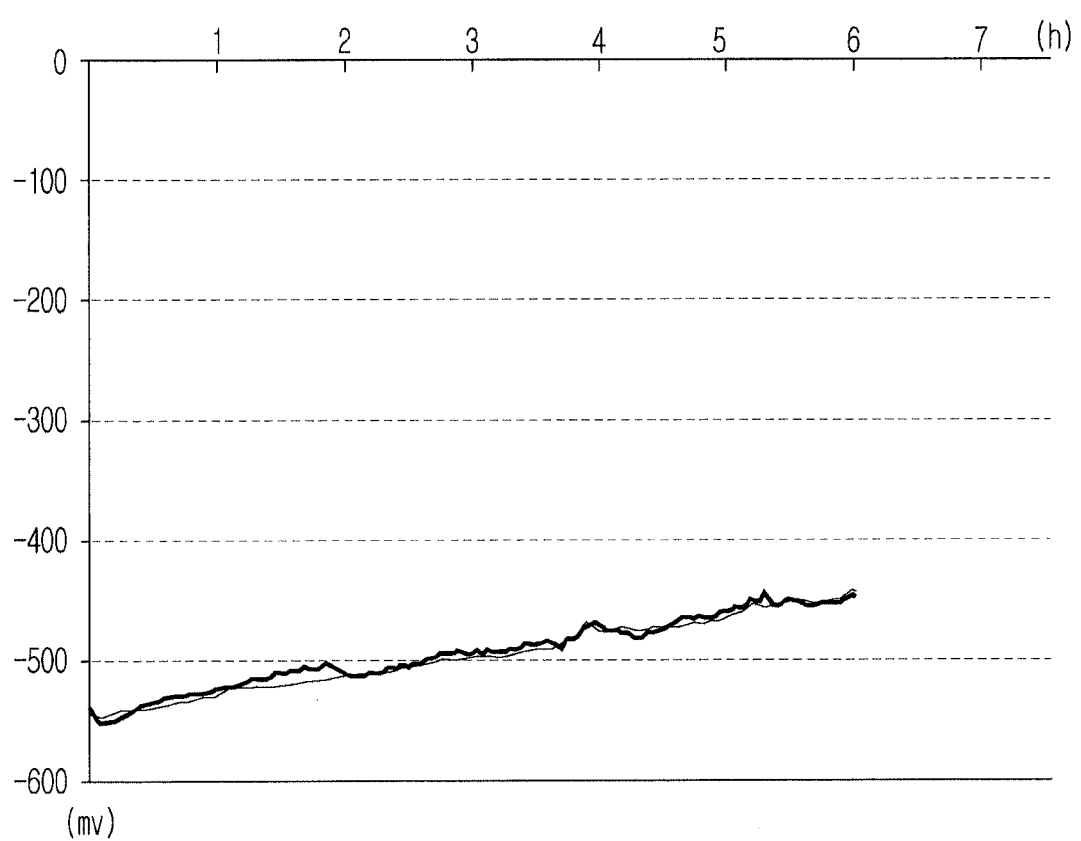

FIG. 11 is a graph showing an oxidation-reduction potential of the platinum electrode oxidation-recycled after immersion for five days shown in FIG. 10 and an oxidation-reduction potential of the platinum electrode oxidation-recycled after immersion for three days.

As can be seen from FIG. 11, the oxidation-reduction potential (thin line) of the platinum electrode oxidation-recycled after immersion for five days, and oxidation-reduction potential (thick line) of a repeatedly oxidation-recycled platinum electrode exhibit substantially equivalent variation behaviors.

That is, as can be seen from FIGS. 8 to 11, although the platinum electrode has a deteriorated measurement performance due to hydrogen atoms adsorbed thereon, the platinum electrode may return to an initial state thereof via an oxidative recycling process, in which a positive voltage is applied thereto, and the platinum electrode maintains the surface state and exhibits the initial measurement performance, although repeatedly undergoing oxidative recycling.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. An electrode system comprising:
   a low porosity platinum working electrode in which platinum is deposited in a porous form on the surface of an electrode;
   a high porosity platinum electrode having a higher roughness factor than the low porosity platinum electrode;
   a reference electrode; and
   a processor configured to calculate a pH of the solution based on a measured potential value between the high porosity platinum electrode, which acts as a working electrode, and the reference electrode and configured to calculate an oxidation-reduction potential of a solution based on another measured potential value between the low porosity platinum working electrode and the high porosity platinum electrode, which acts as another reference electrode.

2. The electrode system according to claim 1, wherein the low porosity platinum working electrode has a roughness factor of about 1 to about 50 and the high porosity platinum working electrode has a roughness factor of about 50 to about 400.

3. The electrode system according to claim 1, wherein the reference electrode is made of gold or silver.

4. The electrode system according to claim 1, wherein the low porosity platinum working electrode and the high porosity platinum working electrode are working electrodes with respect to the reference electrode and the low porosity platinum working electrode is an oxidation-reduction potential (ORP) measurement electrode and the high porosity platinum working electrode is a pH measurement electrode.

5. The electrode system according to claim 1, wherein the low porosity platinum electrode is a working electrode that measures an oxidation-reduction potential of a solution using the high porosity platinum electrode as a reference electrode.

6. The electrode system according to claim 5, wherein the oxidation-reduction potential calculated by the low porosity platinum electrode using the high porosity platinum electrode as a reference electrode is an oxidation-reduction potential based on a dissolved gas present in the solution.

7. The electrode system according to claim 6, wherein the solution is reducing water in which hydrogen gas is dissolved and the dissolved gas comprises a hydrogen gas.

8. The electrode system according to claim 1, a control unit to control a relay to apply a positive potential to one or more of the low porosity platinum working electrode and the high porosity platinum electrode relative to the reference electrode to perform oxidation recycling of the one or more of the low porosity platinum working electrode and the high porosity platinum electrode.

* * * * *